United States Patent [19]

Fallas

[11] Patent Number: 5,512,049

[45] Date of Patent: *Apr. 30, 1996

[54] SYRINGE NEEDLE COVER HOLDER/GRASPER

[76] Inventor: Daryl C. Fallas, 77 Parker Ave., Deal, N.J. 07723

[*] Notice: The term of this patent shall not extend beyond the expiration date of Pat. No. 5,292,313.

[21] Appl. No.: 181,454

[22] Filed: Jan. 14, 1994

Related U.S. Application Data

[63] Continuation of Ser. No. 832,417, Feb. 7, 1992, Pat. No. 5,292,313.

[51] Int. Cl.$^6$ .................................................. A61M 5/32
[52] U.S. Cl. .................................................. 604/192; 604/263
[58] Field of Search ........................... 604/110, 187, 604/192, 197, 198, 218, 263; 128/919; 206/364–366

[56] References Cited

U.S. PATENT DOCUMENTS

| | | | |
|---|---|---|---|
| 4,596,562 | 6/1986 | Vernon | 604/192 |
| 4,846,803 | 7/1989 | Emerson | 604/263 |
| 4,915,698 | 4/1990 | Levenson | 604/192 |
| 4,921,199 | 5/1990 | Villaveces | 248/314 |
| 4,938,514 | 7/1990 | D'Addezio | 294/16 |
| 4,950,015 | 8/1990 | Nejib et al. | 294/19.1 |
| 4,979,945 | 12/1990 | Wade et al. | 604/192 |
| 4,981,476 | 1/1991 | Aichlmayr et al. | 604/192 |
| 5,112,314 | 5/1992 | Aragon et al. | 604/192 |
| 5,143,414 | 9/1992 | Rosellini | 294/99.2 |
| 5,279,578 | 1/1994 | Cooke | 604/192 |

Primary Examiner—C. Fred Rosenbaum
Assistant Examiner—V. Alexander
Attorney, Agent, or Firm—Ezra Sutton

[57] ABSTRACT

Disposable syringes are marketed with a plastic cover which protects the needle assembly inserted within. Typically, the end of the cover that extends towards the barrel of the syringe is designed with a surrounding lip. The holder of the invention is fixed to a surface or stand to receive the cover and grasp, secure or envelop its surrounding lip. In use, the syringe, with its cover, is placed into the holder, slid to one side for the lip of the cover to be grasped, and then the syringe and needle assembly can then be safely pulled away from the cover. To dispose of it, the syringe is reinserted into the grasped cover, then slid with the cover out of the grasp of the holder to the other side, where a pair of nibs are provided to limit its movement and allow for the syringe, with its cover in place, to be lifted out. The holder of the invention makes almost impossible any accidental jabbing of one's fingers or hand in removing the needle assembly from, or inserting it back into, the syringe cover.

9 Claims, 1 Drawing Sheet

SYRINGE NEEDLE COVER HOLDER/GRASPER

This application is a continuation, of application Ser. No. 07/832,417, filed Feb. 7, 1992, now U.S. Pat. No. 5,292,313.

FIELD OF THE INVENTION

This invention relates to the health-care profession, in general, and to disposable hypodermic syringes, in particular.

BACKGROUND OF THE INVENTION

As is well known and understood, perhaps the disease most threatening the world today is Acquired Immune Deficiency Syndrome (AIDS). As is also well known and understood, it is possible to transfer the AIDS virus by its coming into contact with an open wound, cut, or sore. In part, and for such reason, more and more health professionals today wear protective gloves in dealing with patients— whether or not they are known to be AIDS infected.

Analysis has shown, furthermore, that one possible way of transmitting the virus is by the accidental jabbing of one's fingers or hand with the needle of a disposable hypodermic syringe as it is attempted to be inserted back into its protective cover prior to disposal. The opening of the cover to receive the needle is oftentimes of the order of $1/8-3/16$ inches across, and in the active area of a hospital emergency room or medical office, it is not uncommon for one's attention to be diverted elsewhere, and allow the momentary lack of concentration to lead to the inadvertent jabbing.

As will be readily understood, this problem will be seen to follow from the fact that one hand is used to hold the cover, while the other hand is used in an attempt to guide the syringe and needle assembly into proper positioning. On the other hand, and as will be seen from the description below, the apparatus of the present invention provides a "holder" for the cover, which allows the syringe (with its needle assembly) to be reinserted into the cover—as well as being removed from it initially—to be accomplished utilizing only one hand. In such manner, and as will be seen, the accidental jabbing of one's fingers or hand by the needle assembly is prevented.

SUMMARY OF THE INVENTION

As will be seen from the description that follows, the holder of the invention is fixed to a surface or stand in a hospital emergency room, in a doctor's office, in a dentist's office, etc., to receive the cover and grasp the surrounding lip typically provided on the cover at the end which extends over the needle assembly and towards the barrel of the syringe. As will be seen, the holder includes a pair of extension arms to grasp the surrounding lip, one arm above the lip, and the other below the lip. In a preferred embodiment of the invention, the two arms are of a generally U-shape configuration, with the one below the lip being of greater length than the one above the lip. In use—and as will be described—the syringe, with its cover, is placed into the holder, stopped by the lower arm, slid to one side for the lip of the cover to be grasped or secured between the upper and lower arms, and then the syringe can be safely pulled away from the cover, exposing the needle assembly for use. To dispose of the syringe—as will also be described—the syringe is then reinserted into the grasped cover, slid with the cover out of the grasp of the holder to the other side, where a pair of nibs are provided to limit its movement, and allow for the simple lifting of the syringe with its cover in place. As will also be seen, to facilitate the grasping of the surrounding lip, the two extension arms are parallel to each other with the distance between them being equal to that of the lip of the needle cover, which also serves to facilitate the removal of the cover when it is desired to dispose of the syringe after use.

BRIEF DESCRIPTION OF THE DRAWINGS

These and other features of the present invention will be more clearly understood from a consideration of the following description, taken in connection with the accompany drawing in which.

DETAILED DESCRIPTION OF THE DRAWINGS

Figure 1A:
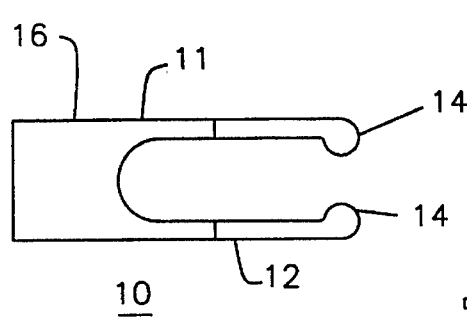
FIGS. 1A and 1B are top and front views, respectively, of a holder for syringe covers constructed in accordance with the present invention.
Figure 1B:
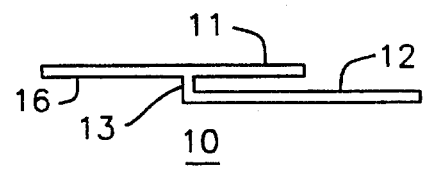

In FIGS. 1A and 1B, the holder 10 is shown as comprising a pair of generally U-shaped arms 11, 12, joined as at 13 but parallel to each other with a separation equal to that of the lip of the needle cover to be described below, and with the arm 12 being longer than the arm 11, of the order of 100%. Arm 12 includes a pair of arms and a pair of extension arms terminating at 14, with the extension arms extending beyond the length of arms 11. The remote end of the arm 12 is shown with a pair of nibs 14, extending inwardly towards one another, to provide a "bent" inward appearance for the arm 12. The opposite ends of the holder 10, as at 16, may be of any desired shape, it being understood that the end 16 is to be secured to a counter surface, a stand, or any other available location in a hospital operating room, medical office, dental office, etc. so as to be held in place without any holding in one's fingers or hand.

Figure 2:
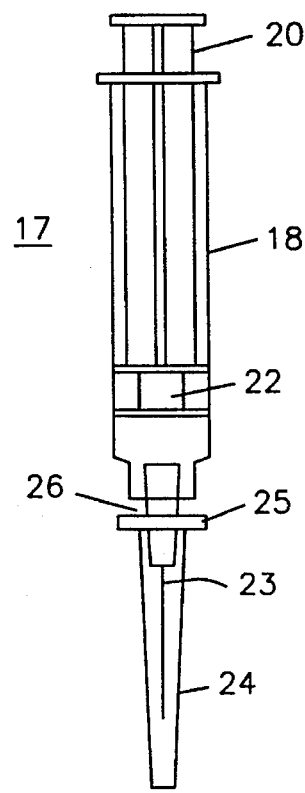
FIG. 2 illustrates a disposable hypodermic syringe usable with the holder of FIGS. 1A and 1B.

FIG. 2 illustrates a hypodermic syringe 17 having a barrel 18, a plunger 20, a stopper 22, a needle assembly 23 inserted into the barrel 18, and a protective cover (24) for the needle assembly typically fabricated of plastic. As will be apparent, the cover 24 is provided with a surrounding lip 25, which just falls short of the barrel 18, as at 26. As is understood, when it is desired to inject the fluid in the barrel 18 into a patient, the protective cover 24 is first removed—and after the fluid is injected by means of the plunger 20, the needle assembly 23 is reinserted into the cover 24, and the syringe 17 is then disposed of. As previously described, and in accordance with the invention, this described use of the syringe 17 will be seen to be accomplished through a one-hand operation only, with the holder of the invention serving to grasp the cover 24 so as to allow easy removal of the syringe from the cover, and the reinsertion of the needle assembly 23 back into position after use.

Figure 3:
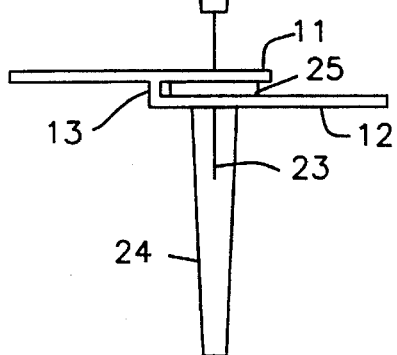
FIG. 3 shows the holder of the invention grasping the syringe cover to allow removal of the syringe and needle assembly for use.
Figure 4:
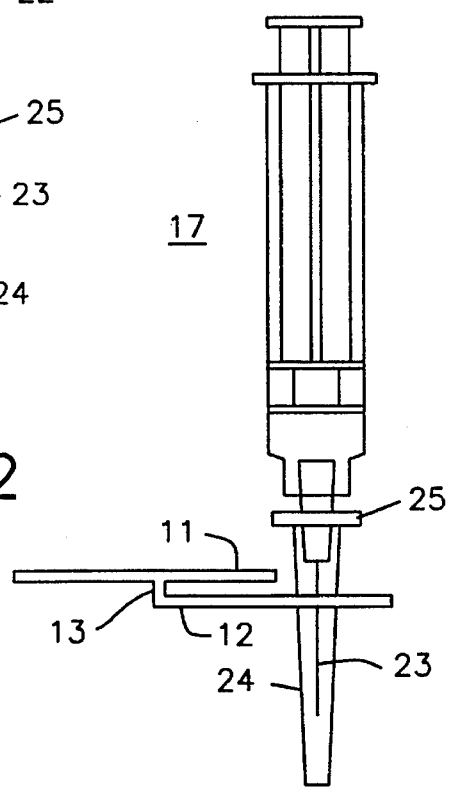
FIG. 4 shows the holder and syringe with the surrounding lip of the cover free from the holder's grasp.

More specifically, and referring to FIGS. 3 and 4, the syringe 17, with its protective cover 24 in place, is first inserted between the U-shaped extensions of the arm 12, and slid to the left, as in the drawings, until such time as the surrounding lip 25 is grasped by the arms 11, 12, which thereupon begin to hold the surrounding lip 25 in place.

Further movement of the syringe 17 to the left then increasingly secures the arms 11, 12 about the lip 25, to hold the cover 24 thus securely in place. The syringe 17, together with its needle assembly, can then be simply lifted away from the holder 10, as by an upwards lifting as shown in the drawing, with the holder 10 then continuing to grasp the cover 24 at that location. The syringe 17 can thus be utilized in its usual manner.

After use, and when it is desired to dispose of the hypodermic syringe 17, with the same hand, it is then repositioned to reinsert the needle assembly 23 back into the protective cover 24, to then slide the syringe 17—now with the cover 24 surrounding the needle assembly—back towards the right, as shown in the drawing. As will be apparent, such movement frees the surrounding lip 25 and cover 24 from the grasp between the arms 11, 12, and continues to move the syringe to the right until hitting up against the nibs 14 or bend in extension arm 12, to limit any further sideways movement of the syringe 17. The syringe can then, again, be simply lifted upwardly, in which event it is removed along with the protective cover 24 surrounding the needle assembly 23. In other words, inserting the syringe 17 between the U-shaped extension arm 12 and sliding it to the left effectively grasps the surrounding lip 25 to enable the syringe to be withdrawn with the needle assembly 23 exposed, and reinserting the needle assembly into the cover 24 and sliding it to the right enables the syringe 17 to be removed with the protective cover 24 back in place, surrounding the assembly 23. Because the holder 10 is always secured to the countertop or other surface, or to any stand, as by fastening to the opposite end 16, the entire operation becomes simply a one-hand generated movement, without any possibility of accidentally jabbing or sticking the fingers or palm of the other hand.

While there have been described what are considered to be preferred embodiments of the present invention, it will be readily appreciated by those skilled in the art that modifications can be made without departing from the scope of the teachings herein of providing a holder for a syringe cover which operates to grasp the surrounding lip of the cover in allowing the syringe and its needle assembly to be both easily removed from the protective cover for use, and to allow its reinsertion for subsequent disposal, all with the use of a one-hand operation to protect against accidental jabbing or sticking. Thus, whereas the arm 12 has been described as being of the order of 100% longer than the arm 11, it will be understood that it only would be that much longer as to provide easy access and generally limited to 200% of the length of the arm 11. It will also be understood that in constructing this, the prongs of the arm 11 need only be long enough for the entire "neck" of the syringe to be surrounded by them. Alternatively, the top and bottom prongs of the arms 11, 12 could be made long enough to accommodate two or more covers on a single unit. In similar manner, the thickness of the upper prongs of the arm 11 is preferably less than the distance between the lip 25 of the syringe needle cover and the syringe/needle assembly 17 so as to allow the cover 24 to be well secured to the assembly when replaced.

It will likewise be appreciated that the present invention will provide its advantageous operation even if the nibs 14 were omitted. Similarly, one might also wish to expand the operation of the invention by providing a "semi-conical" or "semi-funnel" type shape extending upwards from the upper arm 11 or its prongs, facing the nibs 14, to act as a guide for the needle 23 when being reinserted. This, too, will be seen to be within the teachings of the invention.

Furthermore, the invention also is preferably designed with the lower prong of the arm 12 being secured to the end piece 16 in a manner so as to offer a tension or "give" as to allow the arms to bend to accept different thicknesses of lips 25, while still being strong enough to support the weight of the needle assembly being reinserted—although this can be modified as desired. Then, the portion that "gives" can be directly connected to both the upper and lower arms while the upper arm can be constructed with a rear extension which can be fitted into a unit to make it immovable while still allowing for lower prong flexibility.

For at least such reasons, therefore, resort should be had to the claims appended hereto for a true understanding of the scope of the invention.

I claim:

1. A device for removing the cover from and replacing the cover on a syringe and needle assembly by engaging a lip on the cover, comprising:

a) a holder;

b) a first member connected to said holder;

c) said first member having a pair of spaced-apart first arms connected to said holder and a pair of spaced-apart extension arms connected to said first arms, wherein said spaced-apart first arms and said spaced-apart extension arms cooperate to form a guide for guiding the lateral movement of the cover into the space between said first arms;

d) a second member connected to said holder and spaced apart from said first member, said second member having a pair of spaced-apart second arms, wherein said first arms and said second arms are spaced apart to form a receiving area therebetween for receiving and gripping the lip of the cover as the lip is moved laterally along said guide; and e) said first arms including first surface means for engaging one side of the lip and said second arms including second surface means parallel to said first surface means for engaging another side of the lip when the lip is moved into said receiving area, so that the lip is gripped in said receiving area between said first and second arms and the syringe and needle assembly may be moved relative to said holder, with the cover being held by said holder, so that the cover may be removed from or replaced on the syringe and needle assembly.

2. A device in accordance with claim 1, wherein said first arms are parallel to each other and are spaced apart a distance less than the diameter of said lip.

3. A device in accordance with claim 1, wherein said second arms are parallel to each other and are spaced apart a distance less than the diameter of said lip.

4. A device in accordance with claim 1, wherein said first arms and said extension arms together have a longer length than said second arms.

5. A device in accordance with claim 1, wherein said first and second arms are spaced apart at least a distance equal to the thickness of said lip.

6. A device in accordance with claim 1, wherein said device is reusable.

7. A device in accordance with claim 1, wherein said device is disposable.

8. A device for removing the cover from and replacing the cover on a syringe and needle assembly by engaging a lip on the cover, comprising:

a) a holder;

b) a first member having a pair of spaced-apart first arms connected to said holder;

c) a second member connected to said holder and spaced apart from said first member, said second member having a pair of spaced-apart second arms, wherein said first arms and said second arms are spaced apart to form a receiving area therebetween for receiving and gripping the lip of the cover as the lip is moved laterally along said guide; and d) said first arms including first surface means for engaging one side of the lip and said second arms including second surface means parallel to said first surface means for engaging another side of the lip when the lip is moved into said receiving area, so that the lip is gripped in said receiving area between said first and second arms and the syringe and needle assembly may be moved relative to said holder, with the cover being held by said holder, so that the cover may be removed from or replaced on the syringe and needle assembly.

9. A device for removing the cover from and replacing the cover on a syringe and needle assembly by engaging a lip on the cover, the lip having a lower side and an upper side, comprising:

a) a holder;

b) a first member having a pair of spaced-apart first arms connected to said holder;

c) a second member connected to said holder and spaced apart from said first member, said second member having a pair of spaced-apart second arms; and d) said first arms including first surface means for engaging the lower side of the lip when the cover is inserted between said first arms, and said second arms including second surface means parallel to said first surface means for engaging the upper side of the lip when the cover is moved relative to said second arms, so that the syringe and needle assembly may be moved relative to said holder and the cover may be removed from the syringe and needle assembly.

* * * * *